United States Patent
Lederman et al.

(10) Patent No.: US 10,835,710 B2
(45) Date of Patent: Nov. 17, 2020

(54) SEGMENTED MRI CATHETERS AND OTHER INTERVENTIONAL DEVICES

(71) Applicant: The United States of America, as represented by the Secretary, Department of Health and Human Services, Bethesda, MD (US)

(72) Inventors: Robert J. Lederman, Chevy Chase, MD (US); Ozgur Kocaturk, Rockville, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 359 days.

(21) Appl. No.: 15/755,186

(22) PCT Filed: Sep. 14, 2016

(86) PCT No.: PCT/US2016/051600
§ 371 (c)(1),
(2) Date: Feb. 26, 2018

(87) PCT Pub. No.: WO2017/048759
PCT Pub. Date: Mar. 23, 2017

(65) Prior Publication Data
US 2018/0243530 A1    Aug. 30, 2018

Related U.S. Application Data

(60) Provisional application No. 62/219,472, filed on Sep. 16, 2015, provisional application No. 62/326,613, filed on Apr. 22, 2016.

(51) Int. Cl.
*A61B 5/00* (2006.01)
*A61M 25/00* (2006.01)
(Continued)

(52) U.S. Cl.
CPC ........... *A61M 25/005* (2013.01); *A61B 5/055* (2013.01); *A61B 17/00* (2013.01); *A61M 25/00* (2013.01);
(Continued)

(58) Field of Classification Search
CPC ................ A61M 25/00; A61M 25/005; A61M 25/0012; A61M 25/0043; A61M 25/0051;
(Continued)

(56) References Cited

U.S. PATENT DOCUMENTS 5,916,162 A    6/1999  Snelten et al.
6,496,714 B1  12/2002  Weiss et al.
(Continued)

FOREIGN PATENT DOCUMENTS

WO    WO 97/19362    5/1997
WO    WO 00/77926   12/2000
(Continued)

OTHER PUBLICATIONS

Extended European Search Report for related Application No. 16847168.8, dated Mar. 19, 2019, 7 pages.
(Continued)

*Primary Examiner* — Max F Hindenburg
(74) *Attorney, Agent, or Firm* — Sheridan Ross P.C.

(57) ABSTRACT

Disclosed herein are segmented MRI-compatible interventional devices, such as catheters and guidewires, that provide desired mechanical properties while avoiding undesired interactions with MRI fields. Disclosed devices can include helical wires with insulated breaks at intervals along each wire so that the insulated wire segments are individually short enough to avoid substantial resonance and heat being generated in the wires due to an applied MRI field. The segmented wires can be organized into a braided/woven tubular configuration or a non-braided intercalated/parallel
(Continued)

tubular configuration that provides the desired mechanical properties similar to conventional metallic braided catheters. The helical wire segments can be insulated such that the wires do not touch each other at points where they cross over each other. Breaks in the wires can be staggered along the longitudinal axis of the device and/or circumferentially around the device to minimize formation of weak areas where wire breaks are aligned or grouped.

27 Claims, 8 Drawing Sheets

(51) Int. Cl.
 A61B 5/055 (2006.01)
 A61B 17/00 (2006.01)
 G01R 33/28 (2006.01)
(52) U.S. Cl.
 CPC ....... *A61M 25/0043* (2013.01); *G01R 33/287* (2013.01); *A61B 2017/00292* (2013.01); *A61B 2017/00911* (2013.01); *A61M 25/0012* (2013.01); *A61M 25/0045* (2013.01); *G01R 33/285* (2013.01)

(58) Field of Classification Search
 CPC .... A61M 25/0053; A61M 2025/09058; A61M 2025/09108; A61M 2025/09191; A61B 5/055; A61B 17/00
 See application file for complete search history.

(56) References Cited

U.S. PATENT DOCUMENTS

2011/0275951 A1 11/2011 Lips et al.
2014/0052203 A1 2/2014 Bulkes

FOREIGN PATENT DOCUMENTS

WO WO 2010/078552 7/2010
WO WO 2016064753 4/2016

OTHER PUBLICATIONS

International Search Report and Written Opinion for related International Application No. PCT/US2016/051600, dated Dec. 27, 2016, 6 pages.

SEGMENTED MRI CATHETERS AND OTHER INTERVENTIONAL DEVICES

CROSS-REFERENCE TO RELATED APPLICATIONS

This application is the U.S. National Stage of International Application No. PCT/US2016/051600 filed Sep. 14, 2016, which claims the benefit of U.S. Provisional Application No. 62/219,472 filed Sep. 16, 2015, and claims the benefit of U.S. Provisional Patent Application No. 62/326,613 filed Apr. 22, 2016, both of which are incorporated by referenced herein in their entirety.

FIELD

This application relates to interventional devices, such as catheters and guidewires, for use in magnetic resonance imaging applications.

BACKGROUND

Magnetic resonance imaging (MRI) catheterization is a technique to navigate the human body using catheters and other devices under radiation-free guidance in order to accomplish diagnostic or therapeutic procedures. However, MRI catheterization is currently limited by the risk of heating of catheters, guidewires, and other interventional devices that contain metallic elements to provide for mechanical requirements (such as torque control, flexibility, resistance to kinking, and column strength). For example, conventional catheters typically include a woven metallic braid of wires incorporated into a polymeric extrusion to impart these mechanical properties. However, such a woven metallic braid of wires can undesirably interact with MRI to generate strong electrical currents or resonance in the wires, which can produce excess heat that can damage the catheter and injure the patient.

SUMMARY

Disclosed herein are segmented MRI-compatible interventional devices that provide desired mechanical properties while avoiding undesired interactions with MRI fields. Disclosed segmented catheters, for example, can include braided helical wires or non-braided parallel helical wires with insulated breaks at intervals along each wire so that they each comprises a plurality of insulated wire segments that are individually short enough to avoid substantial resonance and heat being generated in the wires due to an applied MRI field. The segmented helical wires can be organized into a tubular configuration, e.g., in a braided and/or spiral coil form, that provides the desired mechanical properties similar to conventional metallic un-segmented catheters. The wire segments can be insulated such that the wire segments do not touch each other at their ends, sides, or at points where they cross over each other. Breaks in the wires can be staggered along the longitudinal axis of the catheter and/or circumferentially around the catheter to minimize formation of weak areas where wire breaks are aligned or grouped. In some embodiments, the helical wires are braided with some of the wires having a first helical handedness or chirality and some of the wires having a second, opposite handedness or chirality. In other embodiments, the helical wires all have the same handedness or chirality such that they are intercalated and extend parallel to each other and do not cross over each other, providing a thinner wall thickness to the catheter. The number of helical wires (e.g., 8 wires or 32 wires braid configurations) and braiding pattern (e.g., diamond, full load pattern, half load pattern, etc.) can depend on the device type.

The foregoing and other objects, features, and advantages of the disclosed technology will become more apparent from the following detailed description, which proceeds with reference to the accompanying figures.

DETAILED DESCRIPTION

Figure 1:
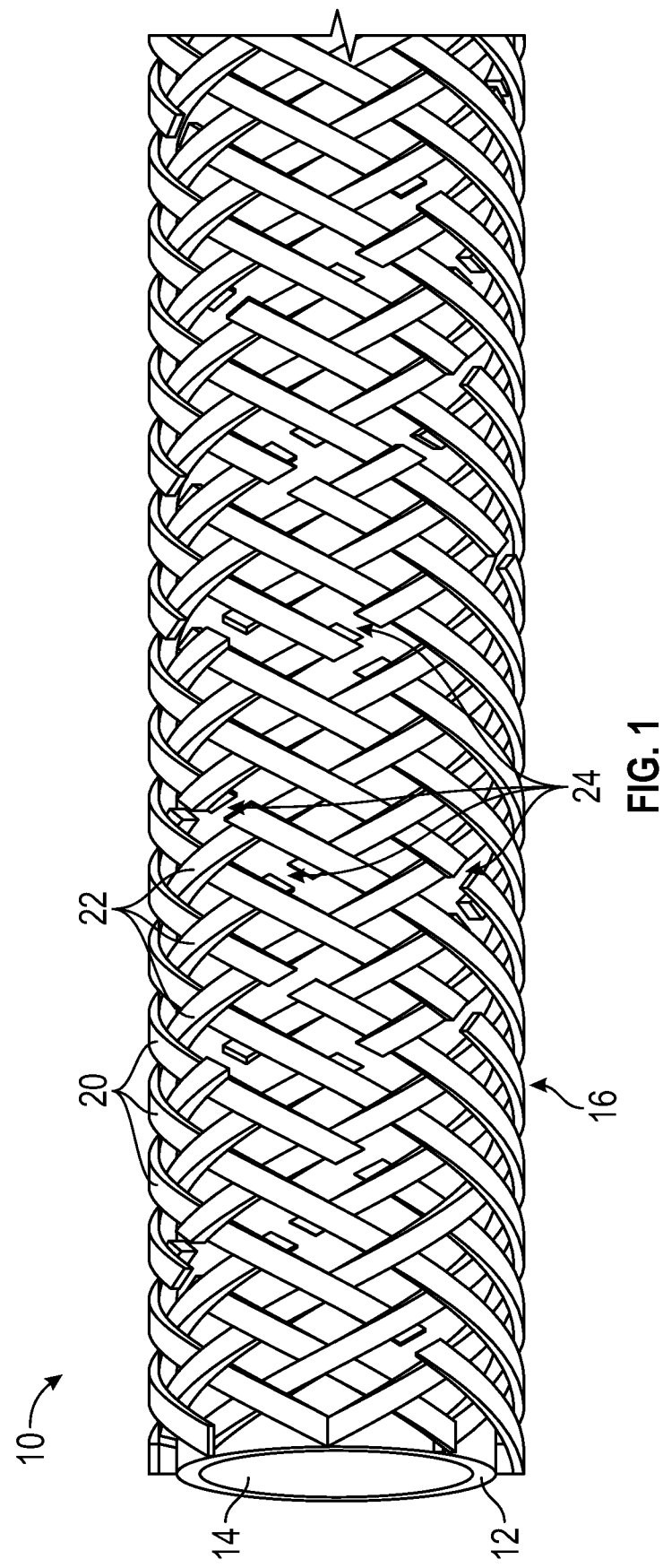
FIG. 1 shows an exemplary three-dimensional wire break pattern for a braided 16-wire segmented MRI catheter.

Disclosed herein are embodiments of interventional devices such as catheters and guidewires for use with MRI that include a plurality of segmented helical wires or coils. Disclosed MRI devices can provide the desired mechanical properties of traditional metallic non-segmented braided devices (e.g., torque control, resilient flexibility, trackability, resistance to kinking, and/or column strength) without undesired interactions that traditional metallic braided catheters have when used with MRI (e.g., without generating undesired levels of resonance and heat). For example, disclosed segmented catheters can include braided or non-braided helical wires with insulated breaks at intervals along the wire so that the catheters comprise a plurality of insulated wire segments that are individually short enough to avoid substantial resonance and heat being generated in the wires due to an applied MRI field. The segmented wires can be arranged in a tubular configuration that provides desired mechanical properties similar to conventional metallic braided catheters, while at the same time being insulated from each other such that the wire segments do not touch each other at their ends, sides, or points where they cross over each other. The wire segments can be arrayed out of phase such that the breaks in the wires are staggered along the longitudinal axis of the catheter and/or circumferentially around the catheter to minimize formation of weak areas where wire breaks are aligned or grouped together.

FIGS. 1-3, 6 and 7 shows examples of 16-wire MRI catheters that include eight "wires" wound in one helical direction (first chirality) and eight wires wound in the opposite helical direction (second chirality) about a common central axis of the catheter, in a braided or woven pattern (e.g., diamond braid pattern). The disclosed technology can be used with catheters having any number of braided or woven wires included in the catheter, such a 24 wires with 12 of each chirality, 12 wires with six of each chirality, eight wires with four of each chirality, or four wires with two of each chirality. It is not necessary to have an even number of wires of each chirality. In some embodiments there are four to 24 total wires of opposite chiralities, for example with a ratio of the number of wires of one chirality to the other being in the range of 0.4 to 0.6.

The disclosed technology can be implemented in other interventional devices, such as guidewires or other elongated transvascular/transluminal devices, for safe use in MRI. For example, in an analogous guidewire embodiment, the same braided/woven wire concepts can be applied, but with a smaller or non-existent inter lumen. Thus, any description provided herein for a catheter can be analogously applied to other MRI-safe tubular devices and to MRI-safe guidewires and other similar non-tubular interventional devices, such as solid, cylindrical and/or rod-shaped devices.

The disclosed technology can be used with devices having any dimensions. In one example, a catheter according to a disclosed embodiment can have an outer diameter of about 0.079 inches and an inner lumen diameter of about 0.045 inches. The wires in the catheter similarly have any thickness. For example, the wires used in the catheter can have a circular cross-section with a diameter of about 0.0025 inches or about 0.0045 inches.

The wires can comprise any sufficiently strong, flexible material, such as various metallic materials (e.g., stainless steel). The wire profile can be round or flat. While the disclosed technology is particularly useful with wires made of electrically conductive metallic materials, it could also be used with wires that are not electrically conductive.

Each of the several wires can be segmented into several wire segments including breaks (e.g., electrical disconnections) at intervals along the length of the wire. The length of each wire segment can be selected based on the properties of the MRI field that the catheter is to be subjected to. Each wire segment can be shorter than a threshold length value associated with the field strength of an MRI field in which the catheter is to be used to avoid undesired interactions with the magnetic field. The threshold length can be selected based on an intended MRI field application such that the catheter is safe for use in the intended MRI filed application (e.g., will not resonate and/or significantly heat up, will not burn and/or injure a patient). The threshold length can be less than an associated resonant length. In some embodiments, the threshold length value can be equal to or less than ¼ of the wavelength of the Larmor frequency in vivo of the intended MRI field. The Larmor frequency is also known as the Larmor precession frequency or processional frequency, and can be defined as the rate of precession of the magnet moment of a proton or of a spin packet under the influence of an applied magnetic field. For example, for use in a conventional 1.5 Tesla MRI field, the wires can include insulated breaks every 10 cm or less, such that each wire segment is 10 cm or less in length (linear length of the helical wire, not the axial length of the catheter itself). Similarly, catheters for use in a 3.0 Tesla MRI field can include wire segments that are 5 cm or less in linear length and catheters for use in a 0.5 Tesla MRI field can include wire segments that are 30 cm or less in linear length.

The breaks along the wires can have various configurations and sizes so long as each wire segment is sufficiently electrically insulated from the adjacent wire segments such that no substantial resonance and associated heating is induced in the wires during the intended MRI procedure. For example, the breaks can comprise gaps, cuts, cut-out portions of the wires, sections of insulating wire material connecting conducting wire sections, and/or other configurations. In some embodiments, the breaks are formed after the wires are braided, after the wires are formed into a tubular configuration, and/or after the wires are incorporated into a polymeric/insulating extrusion. In some methods, the breaks are formed by cutting out sections of the wires using a laser ablation process.

Each wire segment can be sufficiently electrically insulated from other wire segments where the wire segments intersect or overlap each other. The wire segments can be electrically insulated from each other (between their ends and where they overlap), and from other electrically conductive materials (e.g., fluids, tools, tissue) positioned radially inside and outside of the braided wires, in various ways, such as by being encased in one or more layers of polymeric material and/or other insulating material. The wire braid can be encased in a polymeric material either before or after the breaks are formed in the wires. In some embodiments, the adjacent wire segments can be joined via non-conductive material (such as ultraviolet cured glue). In some embodiments, the wires can be individually covered in a first insulating material (e.g., perfluoroalkoxy alkane or other fluoropolymers) prior to being braided, and then the braided wire mesh can be additionally coated or jacketed in a second insulating material (e.g., PEBAX or other polymeric materials). The braided wires can also be covered on the radial inner side and/or radial outer side by layers of material that provide other desired properties for the catheter, such as flexibility, low friction, radial and/or axial strength, biocompatibility, liquid-proofing, perforations, permeability, anti-coagulation, etc.

The disclosed technology can provide for MRI catheters of any axial length and/or any diameter. The axial length of a catheter according to the disclosed technology can correspond to the amount of insulated wire segments included along the length of each wire. In other words, the catheter can be made long or shorted by including more wire segments, without necessarily changing the length of each individual wire segment.

Any of the disclosed embodiments can further include MRI conspicuity markers or features. For example, the catheters can be painted or otherwise applied with an iron oxide suspension at discrete locations along the catheter to create MRI susceptibility artifacts. Disclosed catheters can also be encircled intermittently using resonant coils for inductive coupling. In some embodiments, disclosed catheters can include active resonant receiver coils connected to transmission lines to impart MRI conspicuity.

FIG. 1 illustrates an exemplary three-dimensional wire break pattern for a 16-wire segmented MRI catheter 10. For illustration, the catheter 10 is shown without insulating material and/or other external layers of material that can be applied between and over the braided wires. The catheter 10 is shown with an internal layer of material 12 (e.g., polymeric insulating material) that defines an inner lumen 14 of the catheter. The wire braid 16 of the catheter 10 includes 16 wires, with eight wires 20 having a first helical chirality braided with eight wires 22 having an opposite second helical chirality. The wires 16 each include breaks 14 along their helical lengths. As shown, the breaks 24 can be arrayed out of phase with each other such that the breaks are staggered along the longitudinal axis of the catheter and staggered circumferentially around the catheter to reduce or avoid weakened areas where wire breaks are aligned or grouped together.

In FIG. 1, the wires 16 are shown having a rectangular cross-sectional shape, though this shape is just one exemplary cross-sectional shape the wires can have. In other embodiments, the wires can have various other cross-sectional shapes, such as square, elliptical, circular, polygonal, etc. In some embodiments, different wires in the same braid can have different cross-sectional shapes and/or different thicknesses/diameters.

Figure 2:
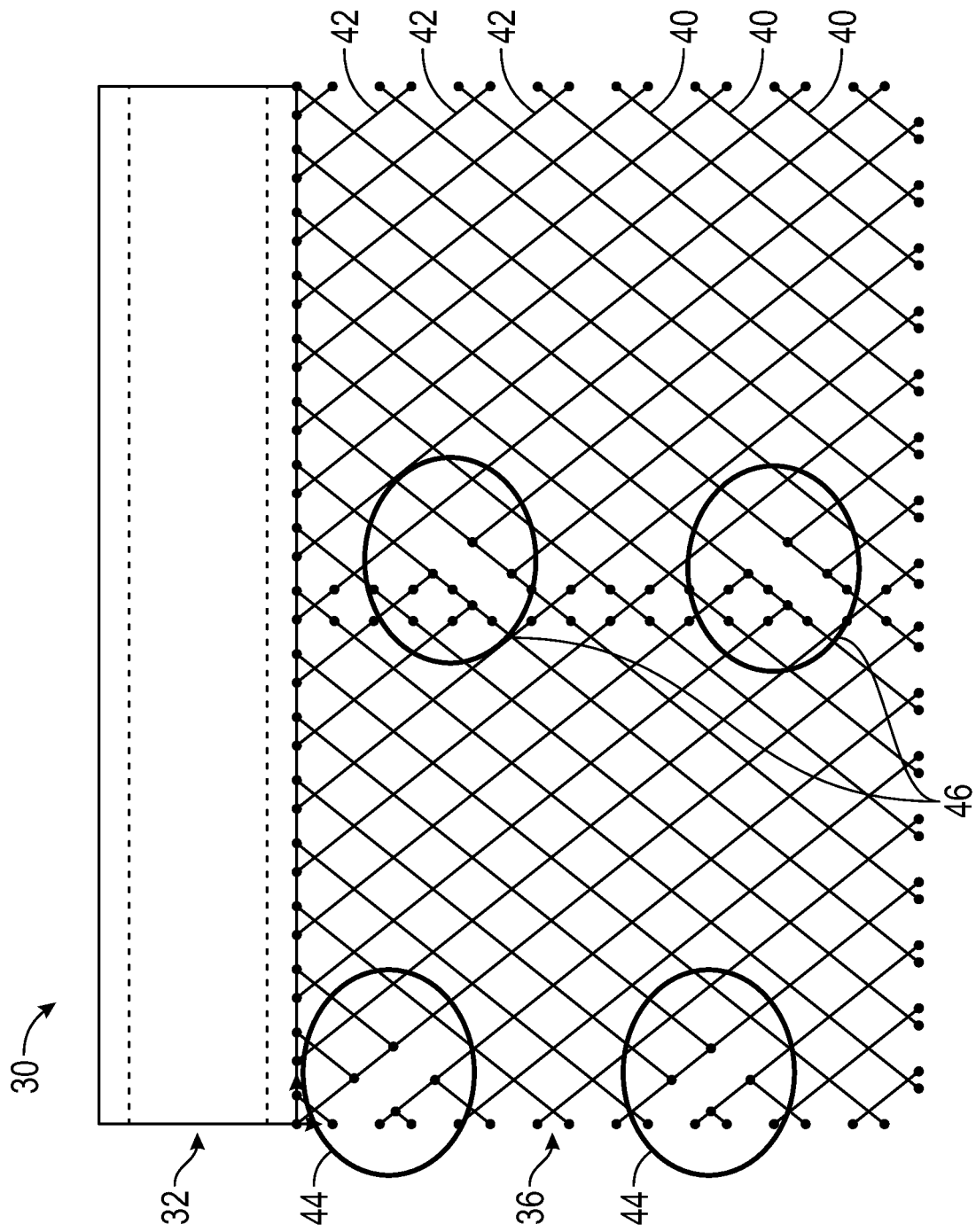
FIG. 2 shows an exemplary two-dimensional wire break pattern for a braided 16-wire segmented MRI catheter.

FIG. 2 is a two-dimensional schematic illustrating a catheter 30 having another exemplary wire break pattern for a 16-wire segmented MRI catheter. The outer diameter of the catheter 30 is shown at 32 for scale and the un-rolled wire braid 36 is shown below. The wire braid 36 includes 16 wires, with eight wires 40 having a first helical chirality braided with eight wires 42 having an opposite second helical chirality. The wires 36 can each include breaks along their helical lengths, as denoted by ovals, or "nodes", 44 and 46 in FIG. 2. Note that the ovals are virtual marks added for illustration only, and not part of the actual catheter. Each node 44, 46 includes two wire breaks in FIG. 2. The breaks in the two nodes 44 are aligned axially with each other but the two groups 44 are spaced apart about 180 degrees circumferentially. Similarly, the breaks in the two nodes 46 are aligned axially with each other, but the two nodes 46 are spaced apart about 180 degrees circumferentially. As shown, the breaks in the nodes 46 are arrayed out of phase axially and circumferentially with the breaks in the nodes 44. The breaks can be included in groups of two, such as in two adjacent wires of the same chirality as shown in FIG. 2, for ease of manufacturing and/or other reasons. In FIG. 2, only eight breaks are illustrated, but additional breaks can be provided following a similar pattern. For example, the pattern shown in FIG. 2 can be continued for twice the axial length shown to create one periodic catheter segment in which each of the 16 wires includes one break.

Figure 3:
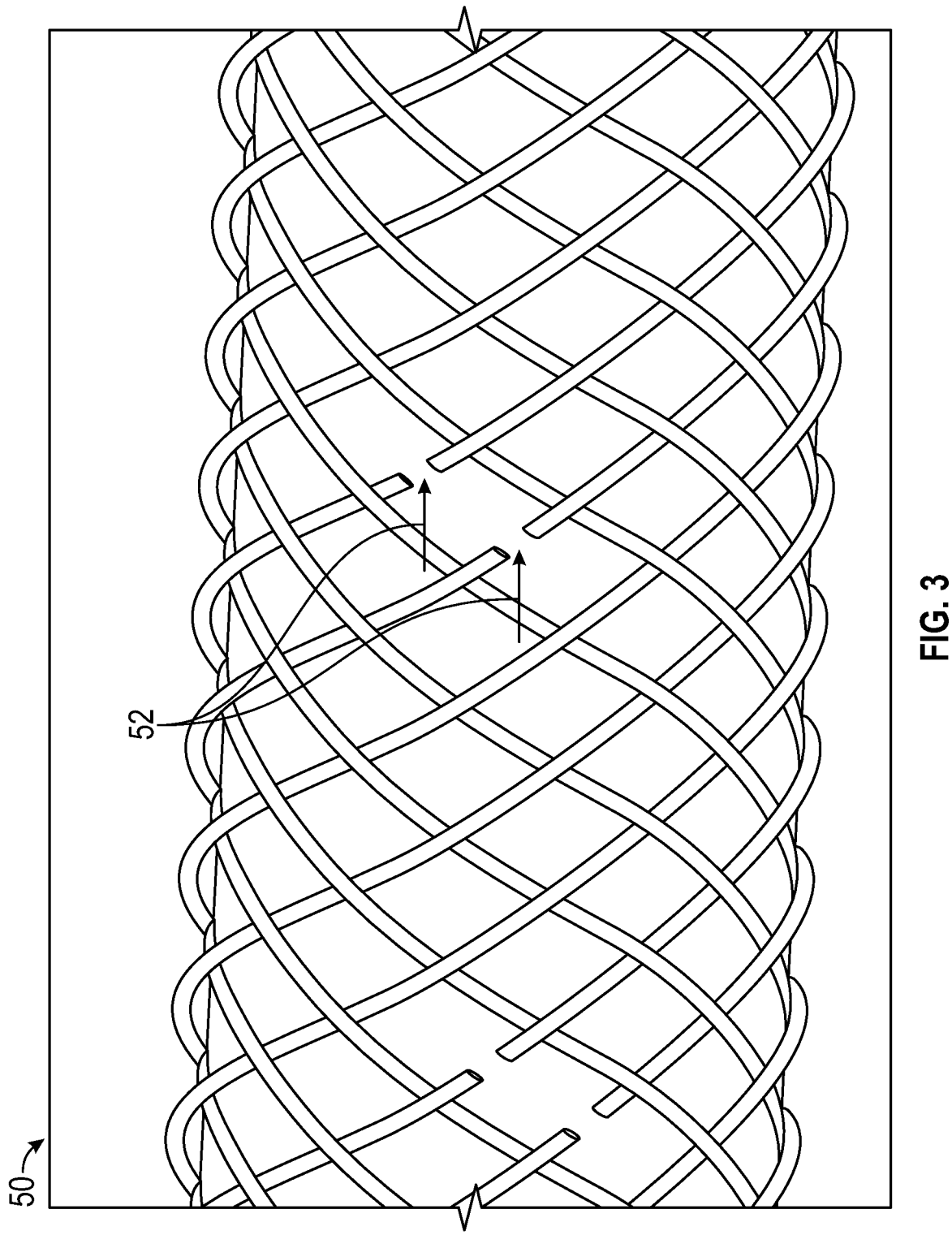
FIG. 3 shows an exemplary braided 16-wire segmented MRI catheter without an outer insulation layer.

FIG. 3 shows an exemplary 16-wire segmented MRI catheter 50 without an outer insulation layer. Two breaks 52 can be seen in adjacent wires of the same chirality, similar to the pattern shown in FIG. 2. In the embodiment of FIG. 3, the braid is such that each wire passes over two wires of the opposite chirality, then passes under two wires of the opposite chirality, then over two, then under two, etc., in a repeating pattern.

Figure 4:
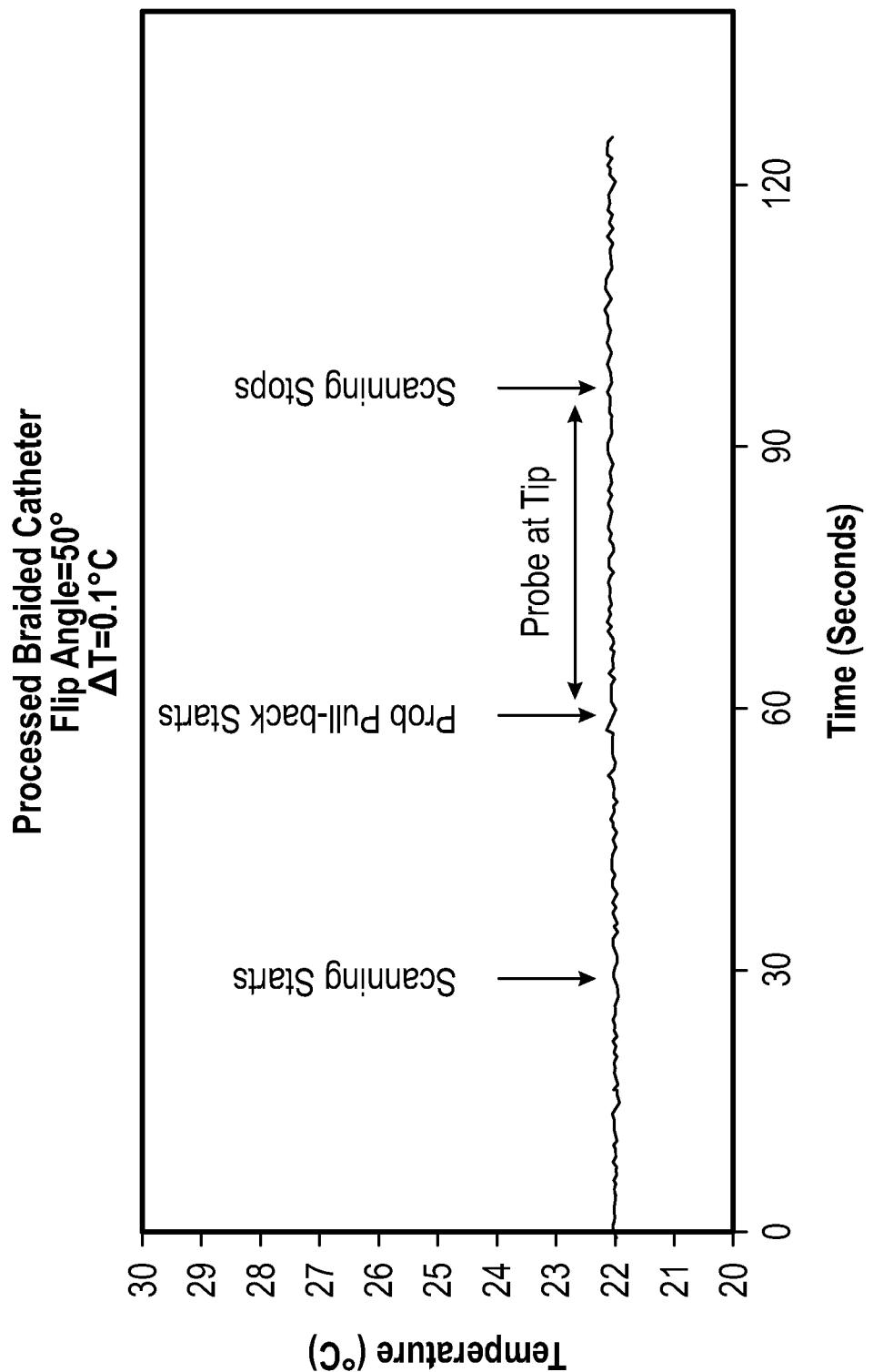
FIG. 4 is a chart illustrating how an exemplary segmented braided catheter does not substantially heat up over time during MRI.

FIG. 4 is a chart illustrating how an exemplary segmented braided catheter does not substantially heat up over time during MRI. The chart of FIG. 4 shows data recorded from a test using a segmented braided catheter having a braid pattern similar to that shown in FIG. 3 with a flip angle of 50 degrees. As shown, the temperature of the segmented catheter does not heat up during MRI scanning, but stays at about 22 degrees C. over an extended time.

Figure 5:
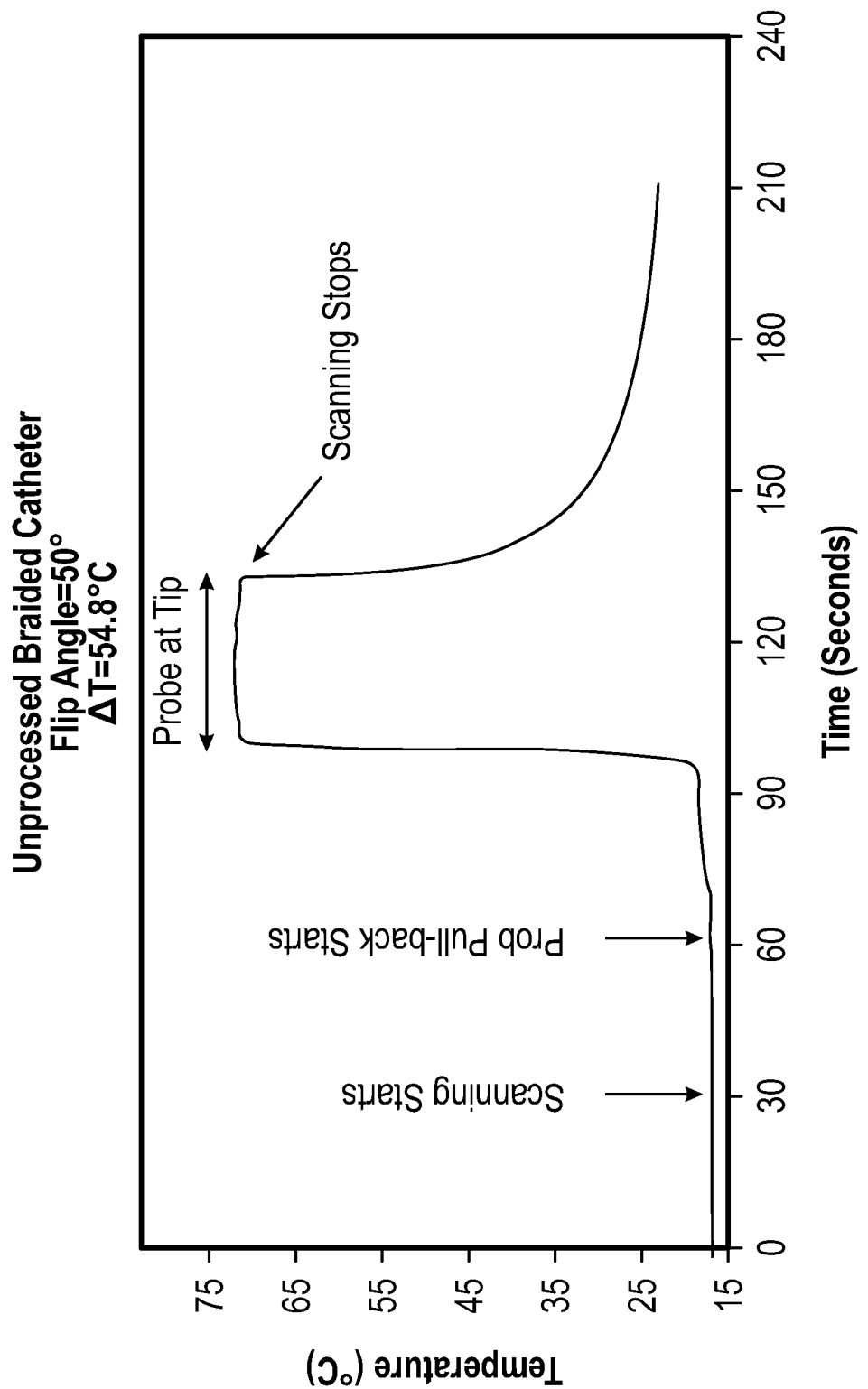
FIG. 5 is a chart illustrating how an exemplary traditional braided catheter does substantially heat up over time during MRI.

FIG. 5 is a chart illustrating how an exemplary traditional braided catheter does substantially heat up over time during MRI. The chart of FIG. 5 shows data recorded from a test using a conventional non-segmented braided catheter having the same braid pattern as the segmented catheter tested in FIG. 4. As shown, the temperature of the conventional catheter heat up significantly (about 55 degrees C.) during MRI scanning.

Figure 6:
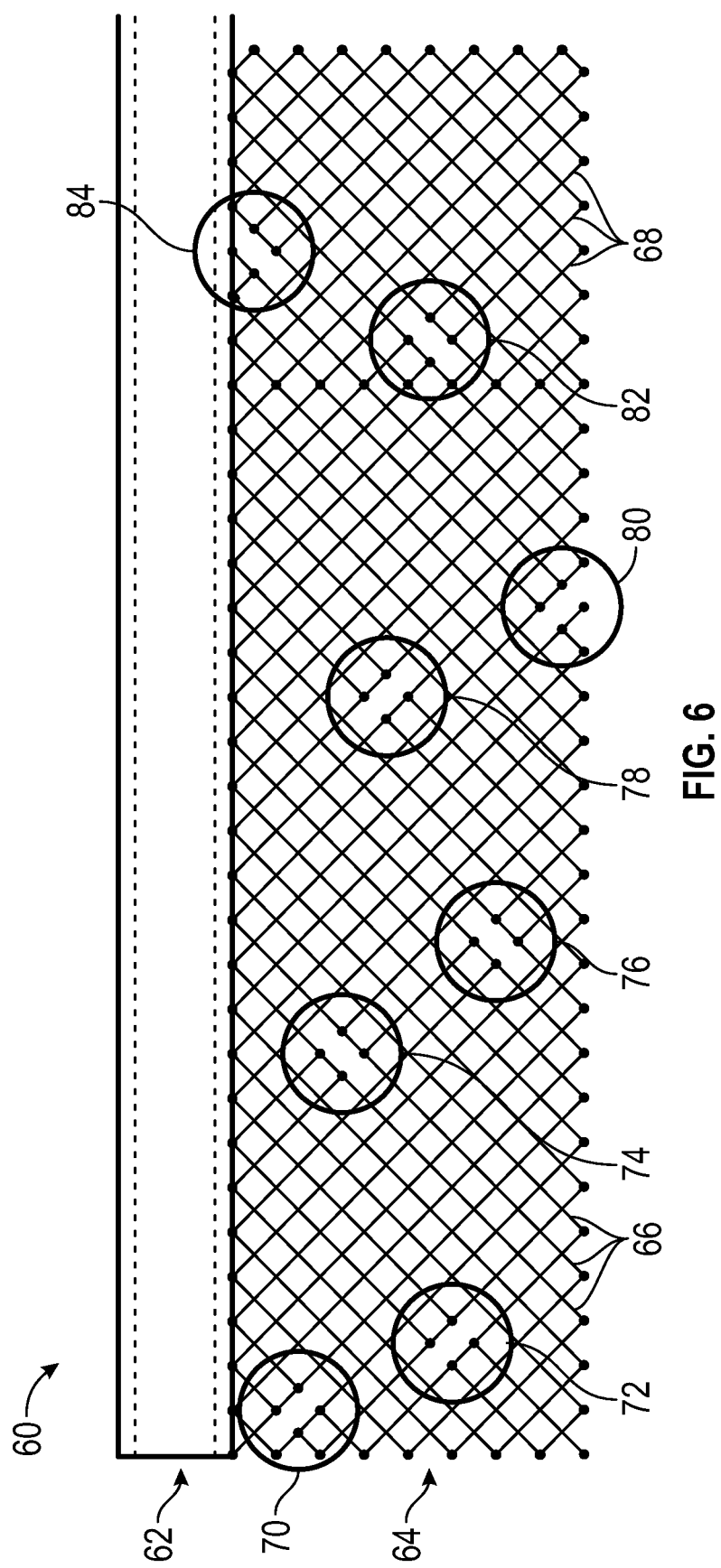
FIG. 6 shows another exemplary two-dimensional wire break pattern for a braided 16-wire segmented MRI catheter.

FIG. 6 is a two-dimensional schematic illustrating a catheter 60 having another exemplary wire break pattern for a 16-wire segmented MRI catheter. The outer diameter of the catheter 60 is shown in solid horizontal lines at 62 and the proportional-sized un-rolled wire braid 64 is shown below for scale. The dashed lines at 62 represent the inner lumen diameter of the catheter 60. The wire braid 64 includes 16 wires, with eight wires 66 having a first helical chirality braided with eight wires 68 having an opposite second helical chirality. The wires 64 can each include breaks along their helical lengths, as denoted by ovals, or "nodes", 70-84 in FIG. 6. Note that the ovals are virtual marks added for illustration only, and not part of the actual catheter. Each of the eight nodes 70-84 includes two wire breaks, such that each of the 16 wires includes one break. Each of the eight nodes 70-84 is axially (left-to-right in FIG. 6) and circumferentially (top-to-bottom in FIG. 6) staggered relative to each of the other nodes, such that they are arrayed out of phase with each other and do not group together to form weak spots. The breaks can be arranged in groups of two per node, such as with breaks in two adjacent wires of the same chirality at each node, as shown in FIG. 6, for ease of manufacturing and/or other reasons.

Figure 7:
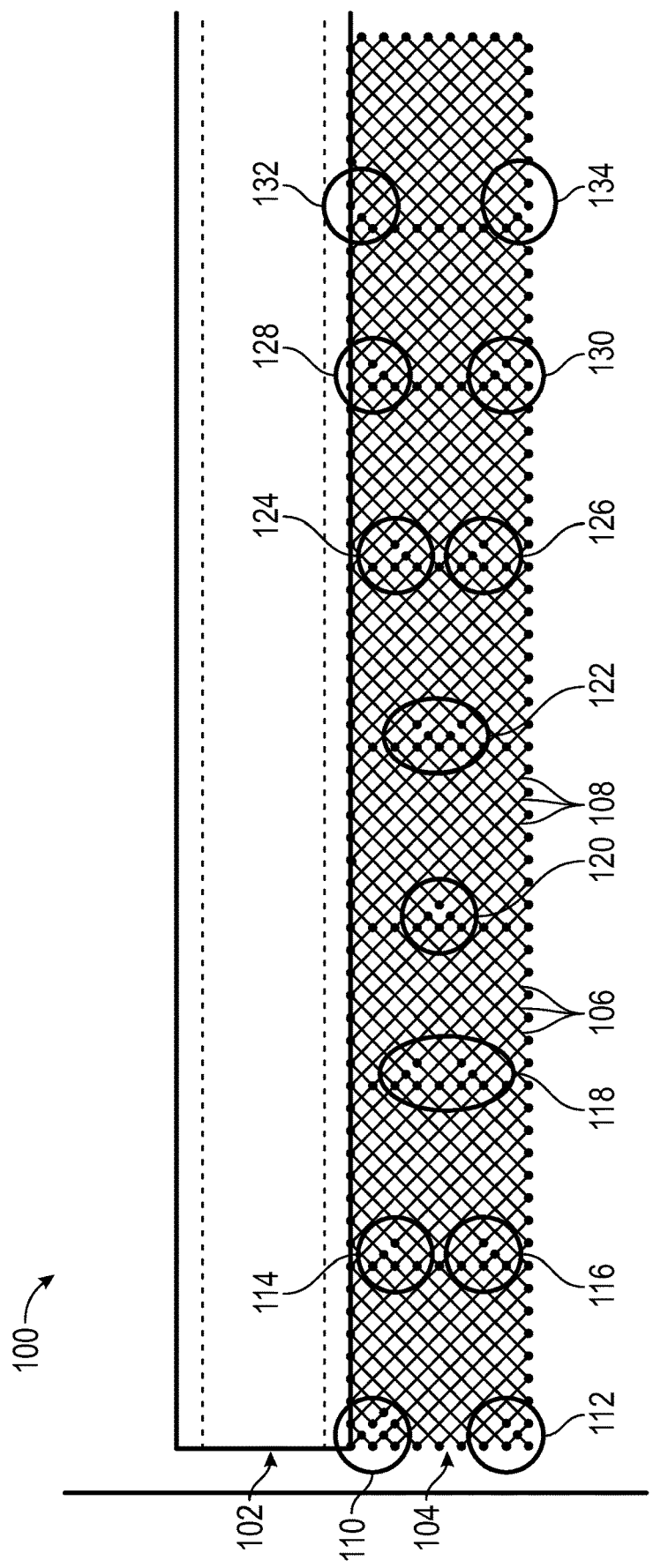
FIG. 7 shows yet another exemplary two-dimensional wire break pattern for a braided 16-wire segmented MRI catheter.

FIG. 7 is a two-dimensional schematic illustrating a 16-wire segmented MRI catheter 100 having yet another exemplary wire break pattern. The outer diameter and inner lumen diameter of the catheter 100 is shown at 102 (solid horizontal lines) and the proportional-sized un-rolled wire braid 104 is shown below for scale. The wire braid 104 includes 16 wires, with eight wires 106 having a first helical chirality braided with eight wires 108 having an opposite second helical chirality. The 16 wires 104 can each include breaks along their helical lengths, as denoted by 13 ovals, 110-134 shown in FIG. 7. 10 of the 13 ovals in FIG. 7 include one wire break, and three of the ovals (118, 120, 122) include two wire breaks, for a total of 16 wires breaks (one break per wire). In this embodiment, the wire breaks are positioned in groups or nodes of one, each separated from the other breaks, except for two of the breaks shown in oval 120 that are adjacent to each other but in wires of opposite chirality. The 16 wire breaks are located at eight different axial positions, with two wire breaks at each axial position. At each axial position, the two wire breaks are in two wires having opposite chirality. At the same time, the 16 wire breaks are located at 16 different circumferential positions, with one wire break at each circumferential position, such that the breaks are all phased with respect to each other. Because the wire breaks in the catheter 100 are separated from each other, rather than in groups of two as in the catheters 30 and 60, the wire braid 104 can provide the catheter 100 with enhanced mechanical properties, such as increased torque response, compared to the catheters 30 and 60.

Figure 8:
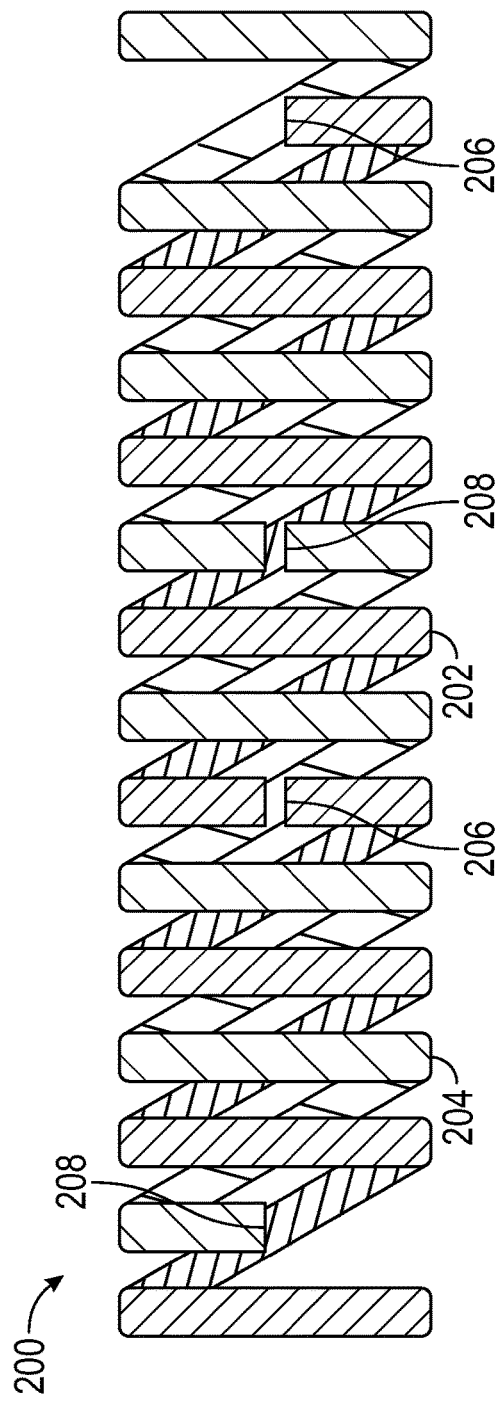
FIG. 8 illustrates a three-dimensional catheter coil pattern that includes two intercalated, parallel, interrupted helical coils having the same helical chirality.

FIG. 8 illustrates a three-dimensional catheter coil pattern 200 that includes two intercalated, parallel, interrupted helical coils 202, 204 having the same helical chirality (e.g., both left-handed helices or both right-handed helices). The term intercalated as used herein means layered or having one element inserted or positioned between two adjacent elements. The term parallel as used herein means parallel in a three-dimensional, helical sense, such that two parallel coils extend in the same direction at points directly adjacent to each other. Though portions of the coils 202, 204 appear non-helical (vertical) in FIG. 8, the illustration is meant to represent true helical coils. The two helical coils 202, 204 run generally parallel to each other with a generally even spacing and do not overlap each other. The coil 202 includes insulated breaks 206 and the coil 204 includes insulated breaks 208. The breaks 206 are offset axially from the breaks 208 to increase mechanical strength (e.g., torquability, column strength, kink resistance) of the catheter. The breaks 206, 208 can also be offset circumferentially from each other.

Figure 9:
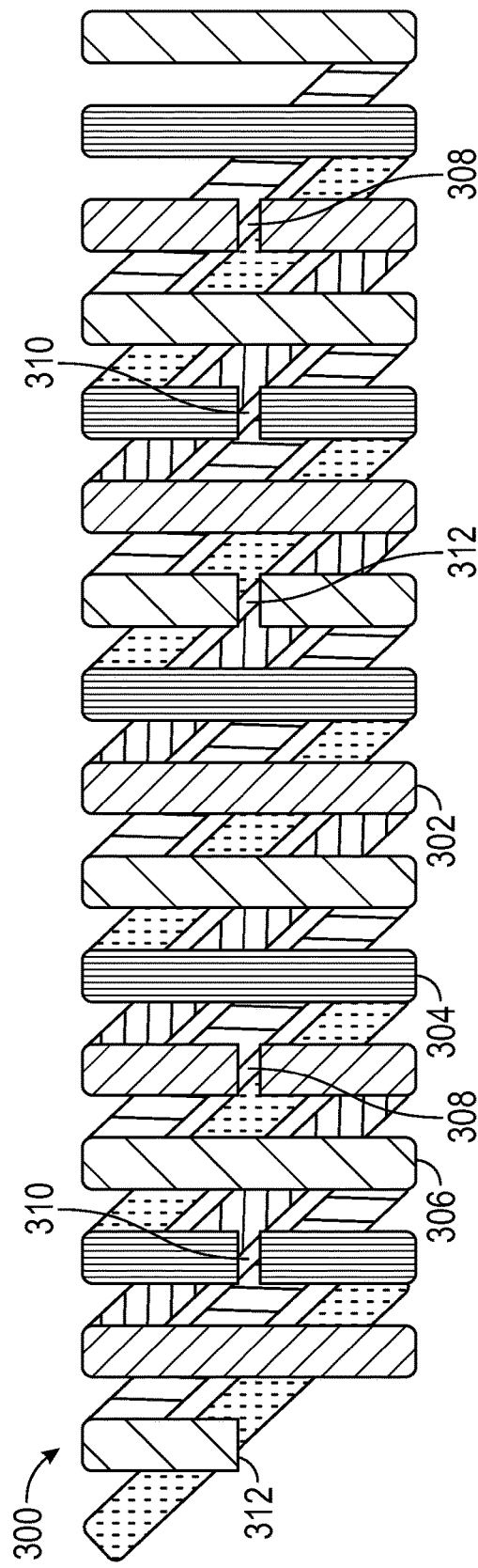
FIG. 9 illustrates a three-dimensional catheter coil pattern that includes three intercalated, parallel, interrupted helical coils having the same helical chirality.

FIG. 9 illustrates a three-dimensional catheter coil pattern 300 that includes three intercalated, parallel, interrupted helical coils 302, 304, 306 having the same helical chirality (e.g., both left-handed helices or both right-handed helices). Though portions of the coils 302, 304, 306 appear non-helical (vertical) in FIG. 9, the illustration is meant to represent true helical coils. The three helical coils 302, 304, 306 run generally parallel to each other with a generally even spacing and do not overlap each other. The coil 302 includes insulated breaks 308, the coil 304 includes insulated breaks 310, and the coil 306 includes insulated breaks 312. The breaks 308, 310, 312 are staggered axially along the catheter to increase mechanical strength (e.g., torquability, column strength, kink resistance) of the catheter. The breaks can also be staggered circumferentially around the catheter.

The embodiments 200 and 300, the linear length of each coil segment between breaks can be less that a predetermined threshold length, as discussed above, to avoid undesired interactions with an applied magnetic field. Also as discussed above, the individual coil segments can be assembled into polymer (or other insulating material) extrusions and/or can be created by forming the breaks after coil extrusion, such as be using laser ablation. Gaps formed at the breaks by laser ablation or other cutting can be filled with polymers or other insulating materials. Because the coils are all parallel and do not overlap, the wall thickness of the catheter can be made thinner, providing an reduced overall outer diameter for the catheter. Coils can be formed from round or flat wires. In alternative embodiments, coils over opposite helical chiralities or other non-parallel helices can be uses such that at least some of the coils overlap each other in some locations. While this can increase the wall thickness of the catheter, it can also provide enhanced mechanical properties for the catheter. In catheter embodiments having coil patterns such as 200 and 300, the total number of intercalated segmented helical wires or coils can be only two (as in 200), only three (as in 300), or more than three.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Any of the claims included in this application are considered to be combinable with any other claim or claims for form combinations claims, all of which combinations are considered to be disclosed herein and supported by this disclosure. For example, and claims that is dependent from just one other claims can alternatively be made dependent from "any one or more of the preceding claims" or the like without departing from the scope of this disclosure.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. An elongated, MRI-compatible, interventional device comprising a plurality of helical wires arranged in an elongated tubular or rod-shaped configuration, the plurality of wires covered by electrically insulating material, wherein each of the plurality of helical wires comprises non-electrically-conductive breaks at intervals along the length of the wire such that the wire is segmented into a plurality of wire segments between the breaks, each wire segment having a length less than a threshold length, and wherein each wire segment is electrically insulated from the other wire segments of the interventional device;

wherein the threshold length is selected based on a field strength of a corresponding MRI field application such that the interventional device is safe for use in the corresponding MRI field application;

wherein the threshold length is less than an associated resonant length for the MRI field application.

2. The interventional device of claim 1, wherein the threshold length is equal to or less than ¼ of a wavelength of a Larmor frequency in vivo of the corresponding MRI field.

3. The interventional device of claim 1, wherein the corresponding MRI field application comprises a 3.0 Tesla MRI field and the threshold length is 5 cm or less, or the corresponding MRI field application comprises a 1.5 Tesla MRI field and the threshold length is 10 cm or less, or the corresponding MRI field application comprises a 0.5 Tesla MRI field and the threshold length is 30 cm or less.

4. The interventional device of claim 1, wherein the wire segments of the interventional device do not substantially heat up when used in the corresponding MRI field application.

5. The interventional device of claim 1, wherein each of the plurality of helical wires is individually covered in insulating material.

6. The interventional device of claim 1, wherein the plurality of helical wires is encased in a tubular insulating material.

7. The interventional device of claim 1, wherein the breaks in the plurality of helical wires are staggered along an axial dimension of the interventional device.

8. The interventional device of claim 1, wherein no more than two breaks in the plurality of helical wires are located at the same axial position along the interventional device.

9. The interventional device of claim 1, wherein each break in the plurality of helical wires is located at a different axial position along the interventional device.

10. The interventional device of claim 1, wherein the breaks in the plurality of helical wires are staggered along a circumferential dimension of the interventional device.

11. The interventional device of claim 1, wherein, in a longitudinal section of the interventional device in which each of the plurality of helical wires includes only one break, each of the breaks is located at a different circumferential position around the interventional device.

12. The interventional device of claim 1, wherein the breaks in the plurality of helical wires are arranged in groups of two adjacent breaks.

13. The interventional device of claim 12, wherein in each group, the two breaks are in two wires having the same helical chirality.

14. The interventional device of claim 1, wherein each of the breaks is separated from the other breaks by at least one of the wire segments.

15. The interventional device of claim 1, further comprising at least one MRI conspicuity marker.

16. The interventional device of claim 1, wherein the plurality of helical wires are arranged in a braided pattern, with a portion of the plurality of wires having a first helical chirality and a portion of the plurality of wires having a second, opposite helical chirality.

17. The interventional device of claim 1, wherein the plurality of helical wires are arranged in a diamond braid pattern.

18. The interventional device of claim 1, wherein the plurality of helical wires comprises at least four wires, with half of the at least four wires having one helical chirality and half of the wires having an opposite helical chirality.

19. The interventional device of claim 16, wherein each wire segment is electrically insulated from each other wire segment that it crosses radially over or crosses radially under.

20. The interventional device of claim 1, wherein the plurality of helical wires have the same helical chirality.

21. The interventional device of claim 1, wherein the plurality of helical wires are parallel to each other.

22. The interventional device of claim 1, wherein the plurality of helical wires do not overlap each other.

23. The interventional device of claim 1, wherein the plurality of helical wires are intercalated with each other.

24. The interventional device of claim 1, wherein the plurality of helical wires comprises only two or three helical wires.

25. The interventional device of claim 1, wherein the interventional device comprises a catheter.

26. The interventional device of claim 1, wherein the interventional device comprises a guidewire.

27. A method comprising:
providing the interventional device of claim 1, and
using the interventional device of claim 1 in an MRI field application without causing substantial heating or resonance of the interventional device caused by the MRI field.

* * * * *